US012788845B2

(12) United States Patent
McCarthy et al.

(10) Patent No.: US 12,788,845 B2
(45) Date of Patent: *Nov. 10, 2026

(54) METHOD FOR MAKING AN INSERTABLE MEDICAL DEVICE WITH A LOW-PROFILE COMPOSITE COVERING USING A DRY PRESSING PROCESS

(71) Applicant: Aran Biomedical Teoranta, County Galway (IE)

(72) Inventors: David McCarthy, County Galway (IE); Tony Durkin, Knocknacarra (IE); Dean King, Knocknacarra (IE); Barry Nugent, Galway City Center (IE)

(73) Assignee: Aran Biomedical Teoranta, Co. Galway (IE)

( * ) Notice: Subject to any disclaimer, the term of this patent is extended or adjusted under 35 U.S.C. 154(b) by 427 days.

This patent is subject to a terminal disclaimer.

(21) Appl. No.: 18/539,953

(22) Filed: Dec. 14, 2023

(65) Prior Publication Data

US 2024/0148935 A1 May 9, 2024

Related U.S. Application Data

(60) Continuation-in-part of application No. 18/142,130, filed on May 2, 2023, now Pat. No. 12,390,554, (Continued)

(51) Int. Cl.
*B29C 43/18* (2006.01)
*A61F 2/24* (2006.01)

(Continued)

(52) U.S. Cl.
CPC ............ *A61L 27/34* (2013.01); *A61F 2/2409* (2013.01); *A61L 33/06* (2013.01); *B29C 43/18* (2013.01);

(Continued)

(58) Field of Classification Search
CPC .......... B29C 43/3642; B29C 2043/106; B29C 2043/3655; B29C 33/54; B29C 43/184; B29C 43/18
See application file for complete search history.

(56) References Cited

U.S. PATENT DOCUMENTS

| | | | |
|---|---|---|---|
| 915,617 | A | 3/1909 | Marsh |
| 3,537,700 | A | 11/1970 | Schenk et al. |

(Continued)

FOREIGN PATENT DOCUMENTS

| | | | |
|---|---|---|---|
| KR | 101567515 | B1 | 11/2015 |
| WO | 2010020660 | A1 | 2/2010 |

(Continued)

OTHER PUBLICATIONS

PCT Written Opinion of the International Searching Authority for International Application # PCT/EP2019/063158; Dated Nov. 24, 2020.

(Continued)

*Primary Examiner* — Matthew J Daniels
(74) *Attorney, Agent, or Firm* — Hodgson Russ LLP

(57) ABSTRACT

A heart valve replacement device and methods of manufacturing same are provided. The heart valve replacement device includes a substrate and a low-profile composite covering in conformal contact with the substrate and suturelessly attached to the substrate. The low-profile composite covering includes a textile base layer and a thermoplastic polymer coating integrated with the textile base layer. The thermoplastic polymer coating or select portions thereof are substantially fluid impermeable.

19 Claims, 6 Drawing Sheets

Related U.S. Application Data which is a division of application No. 16/418,182, filed on May 21, 2019, now abandoned.

(60) Provisional application No. 62/674,139, filed on May 21, 2018.

(51) Int. Cl.
*A61L 27/34* (2006.01)
*A61L 33/06* (2006.01)
*B29L 31/00* (2006.01)

(52) U.S. Cl.
CPC ..... *A61F 2240/001* (2013.01); *A61L 2420/02* (2013.01); *B29K 2713/00* (2013.01); *B29K 2883/00* (2013.01); *B29L 2031/7534* (2013.01)

(56) References Cited

U.S. PATENT DOCUMENTS 4,041,123 A 8/1977 Lange et al.
4,797,085 A 1/1989 Chiang et al.
5,102,604 A 4/1992 Sidles et al.
5,534,287 A 7/1996 Lukic
5,645,559 A 7/1997 Hachtman et al.
5,718,159 A 2/1998 Thompson
5,741,326 A 4/1998 Solovay
5,758,562 A 6/1998 Thompson
5,948,191 A 9/1999 Solovay
5,957,974 A 9/1999 Thompson et al.
5,993,489 A 11/1999 Lewis et al.
6,027,811 A 2/2000 Campbell et al.
6,053,186 A * 4/2000 Moschini ................ B29C 33/52 134/72
6,139,573 A * 10/2000 Sogard ...................... A61F 2/07 623/1.13
6,156,064 A 12/2000 Chouinard et al.
6,159,565 A 12/2000 Campbell et al.
6,245,099 B1 6/2001 Edwin et al.
6,375,787 B1 4/2002 Lukic
6,383,214 B1 5/2002 Banas et al.
6,395,212 B1 5/2002 Solem
6,451,047 B2 9/2002 McCrea et al.
6,488,701 B1 12/2002 Nolting et al.
6,500,203 B1 12/2002 Thompson et al.
6,554,855 B1 4/2003 Dong
6,689,162 B1 2/2004 Thompson
6,733,524 B2 5/2004 Tseng et al.
6,740,115 B2 5/2004 Lombardi et al.
6,752,826 B2 6/2004 Holloway et al.
6,770,087 B2 8/2004 Layne et al.
6,808,533 B1 10/2004 Goodwin et al.
6,911,040 B2 6/2005 Johnson et al.
6,939,372 B2 9/2005 Dong
6,945,991 B1 9/2005 Brodeur et al.
6,981,982 B2 1/2006 Armstrong et al.
7,000,649 B2 2/2006 Takahashi et al.
7,004,966 B2 2/2006 Edwin et al.
7,044,962 B2 5/2006 Elliott
7,048,792 B2 5/2006 Axen et al.
7,052,513 B2 5/2006 Thompson
7,063,721 B2 6/2006 Takahashi et al.
7,186,263 B2 3/2007 Golds et al.
7,198,638 B2 4/2007 Dong
7,297,158 B2 11/2007 Jensen
7,402,174 B2 7/2008 Dong
7,510,571 B2 3/2009 Spiridigliozzi et al.
7,560,006 B2 7/2009 Rakos et al.
7,682,381 B2 3/2010 Rakos et al.
7,691,109 B2 4/2010 Armstrong et al.
7,785,438 B2 8/2010 Jensen
7,828,833 B2 11/2010 Haverkost et al.
7,871,436 B2 1/2011 Ryan et al.
7,914,639 B2 3/2011 Layne et al.
7,935,144 B2 5/2011 Robin et al.
7,939,000 B2 5/2011 Edwin et al.
8,003,180 B2 8/2011 Goffena et al.
8,012,194 B2 9/2011 Edwin et al.
8,034,096 B2 10/2011 Hunt
8,137,605 B2 3/2012 Mccrea et al.
8,221,486 B2 7/2012 Thistle
8,221,505 B2 7/2012 Skerven
8,287,590 B2 10/2012 Whitbourne et al.
8,323,336 B2 12/2012 Hill et al.
8,337,545 B2 12/2012 Osborne
8,343,204 B2 1/2013 Osborne
8,343,207 B2 1/2013 Rakos et al.
8,372,419 B2 2/2013 Hellerbrand et al.
8,403,983 B2 3/2013 Quadri et al.
8,460,366 B2 6/2013 Rowe
8,469,943 B2 6/2013 Bates et al.
8,506,750 B2 8/2013 Hayashi et al.
8,556,962 B2 10/2013 Bates et al.
8,617,337 B2 12/2013 Layne et al.
8,617,441 B2 12/2013 Edwin et al.
8,647,458 B2 2/2014 Banas et al.
8,672,995 B2 3/2014 Blank et al.
8,714,961 B2 5/2014 Micarelli
8,741,201 B2 6/2014 Huang et al.
8,790,241 B2 7/2014 Edwin et al.
8,790,398 B2 7/2014 Paniagua et al.
8,870,949 B2 10/2014 Rowe
8,945,209 B2 2/2015 Bonyuet et al.
8,945,212 B2 2/2015 Bruchman et al.
8,961,599 B2 2/2015 Bruchman et al.
9,056,001 B2 6/2015 Armstrong et al.
9,066,798 B2 6/2015 Osborne
9,078,747 B2 7/2015 Conklin
9,155,616 B2 10/2015 Venkatasubramanian et al.
9,173,737 B2 11/2015 Hill et al.
9,186,240 B2 11/2015 Huang et al.
9,398,947 B2 7/2016 Obradovic et al.
9,427,304 B2 8/2016 Kariniemi et al.
9,492,269 B2 11/2016 Edwin et al.
9,504,568 B2 11/2016 Ryan et al.
9,510,934 B2 12/2016 Liddy et al.
9,522,062 B2 12/2016 Tuval
9,533,072 B2 1/2017 Matheny
9,545,301 B2 1/2017 Wainwright et al.
9,554,898 B2 1/2017 Paniagua et al.
9,572,661 B2 2/2017 Robin et al.
9,615,919 B2 4/2017 Marissen
9,622,862 B2 4/2017 Lashinski et al.
9,642,700 B2 5/2017 Sundler et al.
9,662,206 B2 5/2017 Börtlein et al.
9,730,790 B2 8/2017 Quadri et al.
9,730,794 B2 8/2017 Carpentier et al.
9,782,256 B2 10/2017 Zeng et al.
9,820,851 B2 11/2017 Braido
9,827,090 B2 11/2017 Hill et al.
9,867,697 B2 1/2018 Alkhatib et al.
9,872,765 B2 1/2018 Zeng et al.
9,907,683 B2 3/2018 Zukowski et al.
9,931,193 B2 4/2018 Cully et al.
9,974,649 B2 5/2018 Racchini et al.
10,022,219 B2 7/2018 Bruchman et al.
10,064,745 B2 9/2018 Hossainy et al.
10,070,954 B2 9/2018 Braido et al.
10,085,834 B2 10/2018 Benson et al.
10,085,836 B2 10/2018 Carpentier et al.
10,092,428 B2 10/2018 Faber et al.
10,098,734 B2 10/2018 Hoang
10,149,756 B2 12/2018 Quadri et al.
10,166,097 B2 1/2019 Quadri et al.
10,172,710 B2 1/2019 Drasler et al.
10,179,045 B2 1/2019 Racchini et al.
10,201,417 B2 2/2019 Lin et al.
10,213,298 B2 2/2019 Thambar et al.
10,219,896 B2 3/2019 Sandstrom et al.
10,226,336 B2 3/2019 Beith et al.
10,226,338 B1 3/2019 Rowe et al.
10,231,828 B2 3/2019 Braido et al.
10,231,834 B2 3/2019 Keidar
10,232,564 B2 3/2019 Pelled et al.

(56) References Cited

U.S. PATENT DOCUMENTS 10,238,489 B2 3/2019 Conklin
10,245,141 B2 4/2019 Ghione et al.
10,258,464 B2 4/2019 Delaloye et al.
10,442,143 B2 10/2019 Ono et al.
11,000,631 B1 5/2021 Rose et al.
2001/0002445 A1 5/2001 Vesely
2001/0007956 A1 7/2001 Letac et al.
2001/0010012 A1 7/2001 Edwin et al.
2001/0049555 A1 12/2001 Gabbay
2002/0026238 A1 2/2002 Lane et al.
2002/0032481 A1 3/2002 Gabbay
2002/0052640 A1 5/2002 Bigus et al.
2002/0055773 A1 5/2002 Campbell et al.
2002/0111668 A1 8/2002 Smith
2002/0173842 A1 11/2002 Buchanan
2002/0183834 A1 12/2002 Klaco
2003/0028244 A1 2/2003 Bates et al.
2003/0040792 A1 2/2003 Gabbay
2003/0050694 A1 3/2003 Yang et al.
2003/0109921 A1 6/2003 Moe et al.
2003/0139806 A1 7/2003 Haverkost et al.
2003/0181970 A1 9/2003 Takahashi et al.
2003/0181971 A1 9/2003 Takahashi et al.
2003/0236567 A1 12/2003 Elliot
2003/0236568 A1 12/2003 Hojeibane et al.
2004/0176839 A1 9/2004 Huynh et al.
2004/0182511 A1 9/2004 Rakos et al.
2004/0210305 A1 10/2004 Shu et al.
2005/0096739 A1 5/2005 Cao
2005/0165479 A1 7/2005 Drews et al.
2005/0182486 A1 8/2005 Gabbay
2005/0222675 A1 10/2005 Sauter
2005/0288775 A1 12/2005 Dong
2006/0015167 A1 1/2006 Armstrong et al.
2006/0025857 A1 2/2006 Bergheim et al.
2006/0136052 A1 6/2006 Vesely
2006/0184229 A1 8/2006 Elliott
2006/0195184 A1 8/2006 Lane et al.
2006/0253188 A1 11/2006 Case
2006/0271191 A1 11/2006 Hermansson
2007/0016289 A1 1/2007 Johnson
2007/0023974 A1 2/2007 Wu
2007/0027535 A1 2/2007 Purdy et al.
2007/0135888 A1 6/2007 Khosravi et al.
2007/0162113 A1 7/2007 Sharkawy et al.
2007/0196420 A1 8/2007 Dwyer
2007/0270944 A1 11/2007 Bergheim et al.
2008/0132999 A1 6/2008 Mericle et al.
2008/0147179 A1 6/2008 Cai et al.
2008/0161910 A1 7/2008 Revuelta et al.
2008/0200980 A1 8/2008 Robin et al.
2008/0215144 A1 9/2008 Ryan et al.
2008/0243245 A1 10/2008 Thambar et al.
2009/0005863 A1 1/2009 Goetz et al.
2009/0222082 A1 9/2009 Lock et al.
2009/0294035 A1 12/2009 Layne et al.
2010/0011976 A1 1/2010 Vonesh et al.
2010/0076548 A1 3/2010 Konno
2010/0082094 A1 4/2010 Quadri et al.
2010/0094404 A1 4/2010 Greenhalgh et al.
2010/0137969 A1 6/2010 Rakos et al.
2010/0204781 A1 8/2010 Alkhatib
2010/0249923 A1 9/2010 Alkhatib et al.
2010/0331957 A1 12/2010 Hashi et al.
2011/0029072 A1 2/2011 Gabbay
2011/0040374 A1 2/2011 Goetz et al.
2011/0160846 A1 6/2011 Bishop et al.
2011/0196473 A1 8/2011 Mccrea et al.
2011/0319989 A1 12/2011 Lane et al.
2012/0035722 A1 2/2012 Tuval
2012/0041511 A1 2/2012 Lee
2012/0123529 A1 5/2012 Levi et al.
2012/0296418 A1 11/2012 Bonyuet et al.
2013/0079700 A1 3/2013 Ballard et al.
2013/0085566 A1 4/2013 Forster et al.
2013/0116768 A1 5/2013 Rakos et al.
2013/0131793 A1 5/2013 Quadri et al.
2013/0197625 A1 8/2013 Dwyer
2014/0005772 A1 1/2014 Edelman et al.
2014/0039611 A1 2/2014 Lane et al.
2014/0088697 A1 3/2014 Fogarty et al.
2014/0135911 A1 5/2014 Spenser et al.
2014/0194979 A1 7/2014 Seguin et al.
2014/0209238 A1 7/2014 Bonyuet et al.
2014/0222136 A1 8/2014 Geist et al.
2014/0257466 A1 9/2014 Board et al.
2014/0277422 A1 9/2014 Ratz et al.
2014/0288639 A1 9/2014 Gainor
2015/0119980 A1 4/2015 Beith et al.
2015/0127100 A1 5/2015 Braido et al.
2015/0157458 A1 6/2015 Thambar et al.
2015/0216655 A1 8/2015 Lane et al.
2015/0257882 A1 9/2015 Brtlein et al.
2015/0272738 A1 10/2015 Sievers
2015/0320542 A1 11/2015 Gabriele et al.
2015/0327999 A1 11/2015 Board et al.
2016/0000592 A1 1/2016 Huang et al.
2016/0081783 A1 3/2016 Puckett et al.
2016/0228252 A1 8/2016 Kejdar
2016/0278922 A1 9/2016 Braido et al.
2016/0296325 A1 10/2016 Edelman et al.
2016/0302918 A1 10/2016 Keidar
2016/0317305 A1 11/2016 Pelled et al.
2016/0331530 A1 11/2016 Beith et al.
2016/0339147 A1 11/2016 Cauchon
2016/0346080 A1 12/2016 Righini et al.
2017/0007403 A1 1/2017 Wildhirt et al.
2017/0020667 A1 1/2017 Gainor
2017/0042672 A1 2/2017 Backus et al.
2017/0056155 A1 3/2017 Edwin et al.
2017/0065407 A1 3/2017 Hacohen et al.
2017/0086970 A1 3/2017 Huynh et al.
2017/0172736 A1 6/2017 Chadha et al.
2017/0209264 A1 7/2017 Chau et al.
2017/0252153 A1 9/2017 Chau et al.
2017/0258586 A1 9/2017 Bateman et al.
2017/0296325 A1 10/2017 Marrocco et al.
2017/0296339 A1 10/2017 Thambar et al.
2018/0110617 A1 4/2018 Howard et al.
2018/0125691 A1 5/2018 Folan et al.
2018/0153678 A1 6/2018 Edwin et al.
2018/0200053 A1 7/2018 Alkhatib
2018/0206982 A1 7/2018 Haivatov et al.
2018/0289485 A1 10/2018 Rajagopal et al.
2018/0303597 A1 10/2018 Spindler
2018/0345624 A1 12/2018 Sowinski et al.
2018/0353292 A1 12/2018 Keidar
2018/0360590 A1 12/2018 Li
2018/0360598 A1 12/2018 Bonyuet et al.
2019/0021857 A1 1/2019 Hacohen et al.
2019/0053897 A1 2/2019 Levi et al.
2019/0069903 A1 3/2019 Deshmukh et al.
2019/0083246 A1 3/2019 Hariton et al.
2019/0083247 A1 3/2019 Hariton et al.
2019/0110911 A1 4/2019 Nae et al.
2019/0117369 A1 4/2019 Spindler et al.
2019/0351099 A1* 11/2019 McCarthy ............... A61L 27/48

FOREIGN PATENT DOCUMENTS

WO 2016176441 A1 11/2016
WO 2019036359 A1 2/2019

OTHER PUBLICATIONS

"Medical Insert Molding", Medical Insert Molding in Seaskymedical, URL://www.seaskymedical.com/capabilities/medical-plastic-injection-molding/medical-insert-molding/.

Gateman, Samantha Michelle, et al., "Wear resistant solid lubricating coatings via compression molding and thermal spraying technologies", Surface and Coatings Technology, vol. 426 of Science Direct, Nov. 25, 2021, 1-8.

(56) References Cited

OTHER PUBLICATIONS

"Stent", MedicinePlus, National Institutes of Health/National Library of Medicine, Trusted Health Information for You, URL://medlineplus.gov/ency/article/00203/htm.

* cited by examiner

METHOD FOR MAKING AN INSERTABLE MEDICAL DEVICE WITH A LOW-PROFILE COMPOSITE COVERING USING A DRY PRESSING PROCESS

RELATED APPLICATIONS

This application a continuation-in-part of U.S. patent application Ser. No. 18/142,130, filed on May 2, 2023, which is a divisional of U.S. patent application Ser. No. 16/418,182, filed on May 21, 2019, now abandoned, which claims the benefit of U.S. Provisional Patent Application Ser. No. 62/674,139, filed May 21, 2018, the entirety of which are hereby incorporated by reference for all purposes.

TECHNICAL FIELD

The present disclosure relates to insertable medical devices with low profile composite coverings and methods of manufacturing such insertable medical devices.

BACKGROUND

Blood flow through the human heart is directed through four heart valves: the mitral valve, the tricuspid valve, the aortic valve, and the pulmonary valve. When functioning correctly, these structures act essentially as one-way valves allowing blood to flow forward through the heart, but block blood from flowing backwards. A number of issues can arise within the various heart valves including stenosis (valves not opening sufficiently, typically due to calcification) and regurgitation (the backflow of blood caused by the valve not closing correctly) or a combination of the two, which could necessitate clinical intervention. That intervention may come in the form of surgical replacement of the incompetent heart valve.

Replacement heart valve implants supported by a stent structure can be delivered using catheter-based delivery systems. These prosthetic valves may include expandable stent structures with valve leaflets attached to the inner wall of the stent structure. Replacement heart valves can be crimped down such that it is held on a balloon catheter (e.g., balloon-expandable) or can be contained within the sheath component of a delivery catheter (e.g., self-expanding), and advanced through the vasculature to the target implant site. Once the replacement heart valves is positioned at the target site, the stent structure may be expanded to hold the prosthetic valve firmly in place.

These replacement heart valves are often intended to at least partially block blood flow, and in particular to prevent paravalvular leakage in which blood flows around the valve on the outside of the prosthesis. In order to prevent the occurrence of this issue, replacement heart valves have been developed with skirts covering or partially covering the stent frame structure of the device.

One form of a skirt used for replacement heart valves includes a textile tubular structure constructed by knitting, braiding, weaving or any non-woven textile technique processing yarn fibers into a tubular configuration. Tubular textile structures have the advantage of being naturally porous, which allows desired tissue ingrowth and assimilation into the body. This porosity, which allows for ingrowth of surrounding tissue, is balanced with fluid impermeability to minimize leakage through the body of the skirt. While designing these skirts to minimize permeability it has been necessary to increase the thickness of the textile, providing a highly dense knit or woven construction. In addition, this tight textile construction by its nature reduces the flexibility of the graft material which affects the ability of the stent to which it is attached to crimp and expand unless there is sufficient slack in the textile component. The thickness of the crimped device also impacts the delivery system leading to either an open procedure or a large diameter catheter. A larger catheter can result in a surgeon having fewer options for approaching the target site due to more limited maneuverability.

SUMMARY

Disclosed herein are insertable medical devices with low profile conformal coverings. In aspect, a heart valve replacement is provided that can comprise a substrate and a low-profile composite covering that is in conformal contact with the substrate and suturelessly attached to the substrate. The low-profile composite covering can include a textile base layer fabricated from a material that provides strength to the low-profile composite covering and a substantially fluid impermeable thermoplastic polymer coating integrated with the textile base layer. The composite covering can cling, conform, and adhere to a complex shaped substrate, can be substantially flush with the substrate, and can conform substantially to the exact shape of the substrate. The composite covering can have a thin wall while remaining substantially fluid impermeable. The composite covering can be heat stabilized into the shape of the substrate and pressed and heated onto the substrate with either soft or granule tooling.

In another aspect, a method of manufacturing a heart valve replacement is provided. Such a method comprises obtaining a substrate of an artificial heart valve, heat stabilizing a textile material, coating the textile material with a thermoplastic polymer, attaching the polymer coated textile material to the substrate to form a composite covering on the substrate, and laminating the composite covering to the substrate.

DETAILED DESCRIPTION OF THE DRAWINGS

As used herein with respect to a described element, the terms "a," "an," and "the" include at least one or more of the described element including combinations thereof unless otherwise indicated. Further, the terms "or" and "and" refer to "and/or" and combinations thereof unless otherwise indicated. By "substantially" is meant that the property or characteristic of the disclosed element need not have the exact described property or characteristic but can have a property or characteristic that is recognizable by one skilled in the art as generally or approximately having the described property or characteristic. Insertable medical devices and components thereof as disclosed herein are used for medical purposes and therefore are sterile. With reference to the composite covering and the substrate of an insertable medical device, "conformal contact" means the composite covering is substantially form-fitting to the substrate such that it conforms to substantially the exact shape of the substrate. A low-profile composite covering has a profile that conforms to the substrate such that the choice of the medical device diameter is not affected or compromised. By "integral" or "integrated" is meant that the described components are not separable using a normal amount of force without damaging the integrity (i.e., tearing) of either of the components. A normal amount of force is the amount of force a user would use to remove a component meant to be separated from another component without damaging either component.

Figure 1:
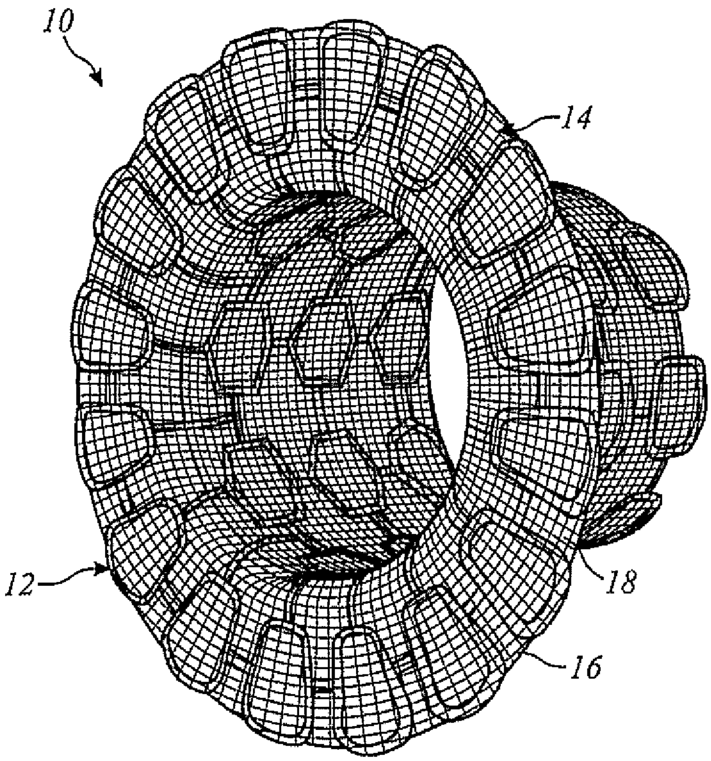
FIG. 1 is a perspective view of a heart valve replacement according to an aspect of the present disclosure.
Figure 2:
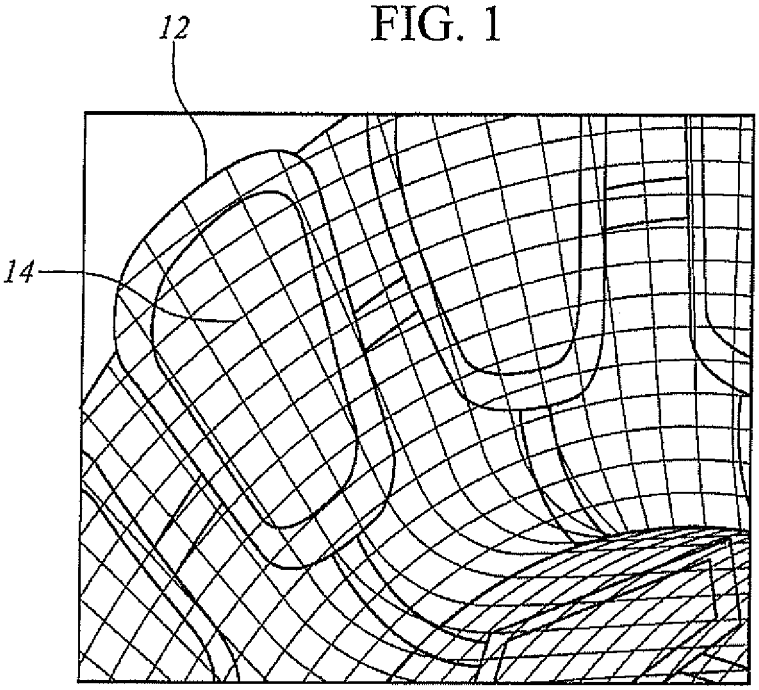
FIG. 2 is a close-up view of part of a heart valve replacement according to an aspect of the present invention.

Disclosed herein are insertable medical devices with low profile conformal coverings. Referring to FIG. 1, in an aspect, an insertable medical device 10 comprises a substrate 12, such as a stent frame, and a low-profile composite covering 14. The composite covering can be in conformal contact with the substrate and directly attached to the substrate such that sutures are not required to attach the composite covering to the substrate. This conformal contact is illustrated in FIG. 2, which is a close-up view of the composite covering 14 clinging to and substantially flush with substrate 12. The composite covering can comprise a textile base layer 16 and a thermoplastic polymer coating 18 integrated with the textile base layer 16. Alternatively, the polymer could be coated onto the frame as well as the textile or coated only on the frame. The textile base layer can provide strength to the composite covering whereas the polymer coating can provide fluid impermeability to the composite covering to create a substantially impermeable seal against leaks or backflow of fluid, such as blood. With respect to the latter, a substantially impermeable surface on the substrate or select regions of the substrate can improve medical device functionality such as, for example, minimizing or preventing paravalvular leakage and type I endoleaks. The composite covering can have a low profile, low bulk, high strength construction while maintaining and maximizing the burst strength and/or suture retention strength of the base textile layer. The base textile layer can have larger porosity for added flexibility. Such composite coverings can allow a smaller diameter delivery system to be used to deliver the medical device, which poses less risk of trauma to the patient during insertion of the medical device. In particular, such composite coverings can reduce the overall packing volume of an implantable medical device to allow easier deployment and use of a smaller diameter catheter (e.g., under 30 Fr). Smaller puncture or insertion sites can also result in reduced recovery time for patients. Further, in the case of cardiovascular uses, when crossing through the septum in the heart, the smaller packing volume can allow for a smaller puncture or insertion site, which does not require repair with a secondary implant. This, in turn, allows for follow up surgery through the same insertion site, which a heart patch would preclude. Smaller delivery systems can also allow surgeons to reach more difficult locations, for example, in the peripheral and neurovascular systems of the patient. The low profile of the composite covering can be based on, for example, the thickness of the composite covering, the reduction or elimination of sutures to attach the composite covering to the textile base layer, and reduced creasing during crimping of the medical device onto the delivery device due to the conformity of the thin composite fabric to the frame and the compliance of the fabric. For example, the composite covering can have a thickness of between about 15 μm and about 250 μm.

The substrate can be fabricated from a metallic or polymeric material. It can have a non-tubular shape, a shape different than a coronary stent and typical of a heart replacement valve, and/or a shape with a non-uniform outer diameter. The textile base layer can be fabricated from a biocompatible, high performance, high tenacity (from about 3 to about 100-gram denier) material extruded as either a monofilament or multifilament yarn. Such monofilament or multifilament yarns can be an implantable grade resorbable or non-resorbable polymer material or a mixtures of such materials and yarn materials including, for example, polyesters, including PET polyesters, polypropylenes, polyurethanes, polytetrafluoroethylenes, polyethylenes including ultra-high-molecular-weight polyethylenes, regenerated silk, nylon, liquid crystal polymer, polyether block amide, and suitable combinations thereof. In the case of multifilament yarns, the yarns can be further processed to increase performance through imparting twists into their structure. The textile base layer can be symmetrically attached to the substrate and configured to expand and contract uniformly with the deployment of the medical device. The textile base layer can be seamless and can be fabricated using, for example, circular, weft, double-needle bed warp knitting, weaving, braiding or any non-woven textile technique processing yarn fibers into a tubular configuration. The polymer coating of the composite covering can comprise a thermoplastic polymer such as, for example, thermoplastic polyurethanes, silicone elastomers, polyurethane-silicone copolymers, polytetrafluoroethylene, fluorinated ethylene/propylene, perfluoroalkoxy fluorocarbon, ethylene/tetrafluoroethylene copolymer and other fluoropolymers, polycarbonate urethanes, polyethylenes, polyamides, polyimides, polyesters, polypropylenes, polyfluoroethylenes, fluorinated polyolefins, fluorinated ethylene copolymer and polyvinylpyr, resorbable polymers such as lactide, glycolide, caprolactone and their co-polymers, polyhydroxybutyrate, polydioxanone, and suitable combinations thereof. The composite covering can be used to bond the composite covering onto the substrate, reducing or eliminating the need for sutures to attach the composite covering to the substrate. The polymer coating can be selectively treated to allow or inhibit tissue integration depending on the desired application of the medical device.

The textile base layer and polymer coating can be a single layer or double layer laminate as described in more detail below. The polymer coating can be integrated with the entire textile base layer or can be integrated with select portions of less than the entire textile base layer such that the textile base layer is selectively uncoated. This may be desired to allow improved tissue ingrowth and integration. The textile fabric layer's porosity, together with an appropriate polymer coating material can be designed to maximize integration of the polymer coating and allow increased areas for lamination in embodiments where the textile fabric layer and polymer coating are a laminate, while minimizing impact on the burst strength and suture retention strength of the medical device. Increased suture retention strength can allow for a more secure attachment of the textile base layer to the target site in the patient's body. The composite covering can be shape-formed to substantially match the implant substrate geometry. The entire composite covering can be porous or non-porous. Alternatively, select portions of the composite covering can be porous or non-porous. For example, select portions of the composite covering can be non-porous to be substantially impermeable to fluid flow, such as blood flow, while other select portions can be porous to promote tissue in-growth. The composite covering can be attached to the entire substrate or can be attached to select portions of less than the entire substrate. For example, as illustrated in FIG. 1, the composite covering 14 can be attached to at least a portion of the outer surface 14*a* of the substrate. The composite covering can also be attached to at least a portion of the inner surface 14*b*. The composite covering or the polymer coating can have pharmaceutical agents incorporated therein. For example, a secondary coating process can be used to incorporate pharmaceutical agents into the composite coating. The insertable medical device or components thereof, such as the composite covering or the polymer coating, can also have other types of surfaces such as, for example, an anti-thrombogenic surface, a hydrophilic surface, or a hydrophobic surface.

Non-limiting examples of insertable medical devices include implantable medical devices such as, for example, peripheral, coronary, and neurovascular implantable medical devices. Non-limiting examples of implantable medical device include heart valve replacement and repair implants (e.g., aortic, mitral, tricuspid, and pulmonary); vascular occlusion devices; vascular, (including venous) stents, and grafts; and other types of short or long term or permanent implantable devices. Insertable medical devices, including implantable medical devices, also include gastrointestinal, pulmonary/endobronchial, urinary, and interventional access devices including catheters.

Figure 3:
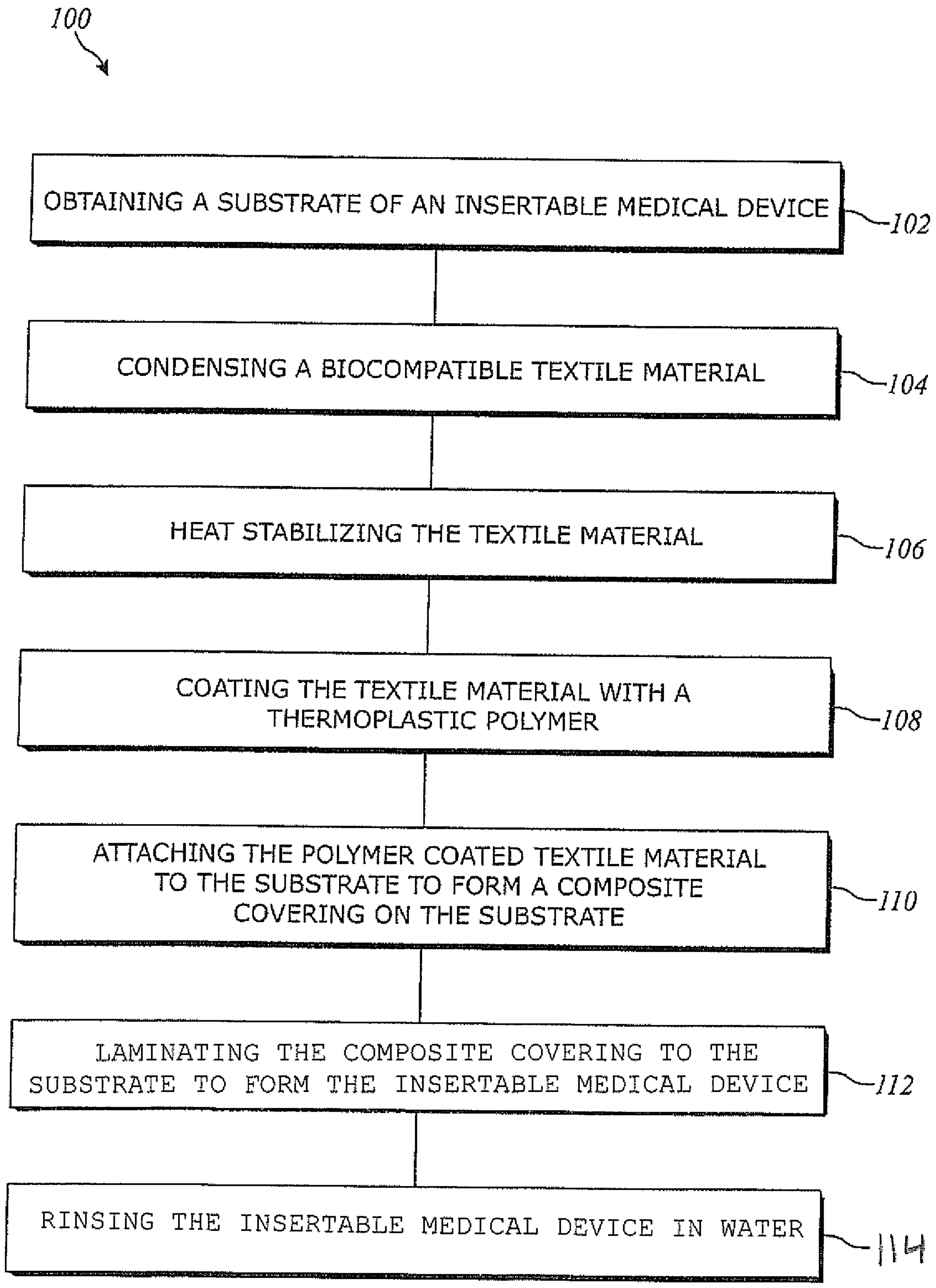
FIG. 3 is a block diagram of steps of an exemplary method of manufacturing an insertable medical device according to an aspect of the present disclosure.

In an aspect, the present disclosure provides methods of manufacturing an insertable medical device. Referring to FIG. 3, a method 100 can include obtaining a substrate, such as a frame having a shape and configuration typical of heart valve replacements, of an insertable medical device 102, optionally condensing a biocompatible textile material 104 and heat stabilizing the textile material 106. Heat stabilization can involve heat treatment of the textile material such that it imparts a pre-determined shape to the textile material. For example, the textile material, constructed to a diameter less than the lowest diameter of a shaped mandrel, can be mounted onto the shaped mandrel such that the soft/greige material of the textile forms around the shape of the mandrel. The mandrel can then be exposed to a heat source, such as placed in an oven, at a temperature above the softening temperature of the textile material. The textile material can then be allowed to cool. Once cooled, if the textile is removed from the mandrel, it will retain the shape of the mandrel, and as such, has been heat stabilized or heat set. Method 100 can further include coating the textile material with a thermoplastic polymer 108. The polymer coated textile material can then be attached to the substrate to form a composite covering on the substrate 110. The polymer coated textile material can be attached to the substrate using a combination of heat and pressure. Prior to attachment, the substrate can be primed or treated to increase the bond strength of the polymer coated textile material to the substrate. Treatments include, for example, surface roughening, use of molecular crosslinkers such as a silane linkage material, use of an intermediate material that bonds more securely to the substrate surface than the textile material and more securely to the polymer coating than the substrate surface. Method 100 can further include laminating the composite covering to the substrate 112 via heat and pressure, for example, to form the insertable or implantable medical device. The lamination process can involve laminating the covering either to the substrate only or, where there are spaces in the structure of the substrate, to itself and around and through the substrate. Selective portions of the substrate can be unlaminated.

Figure 4:
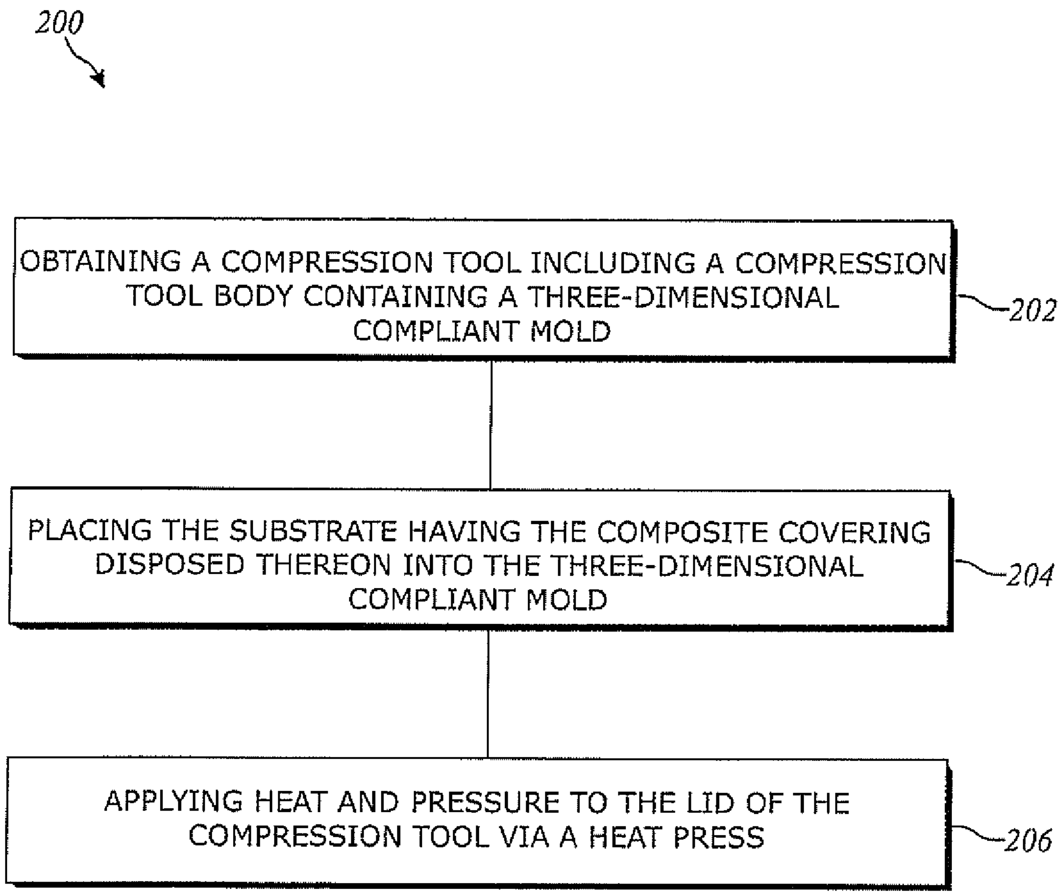
FIG. 4 is a block diagram of steps of an exemplary method of laminating a component of an insertable medical device to another component according to an aspect of the present disclosure.
Figure 5:
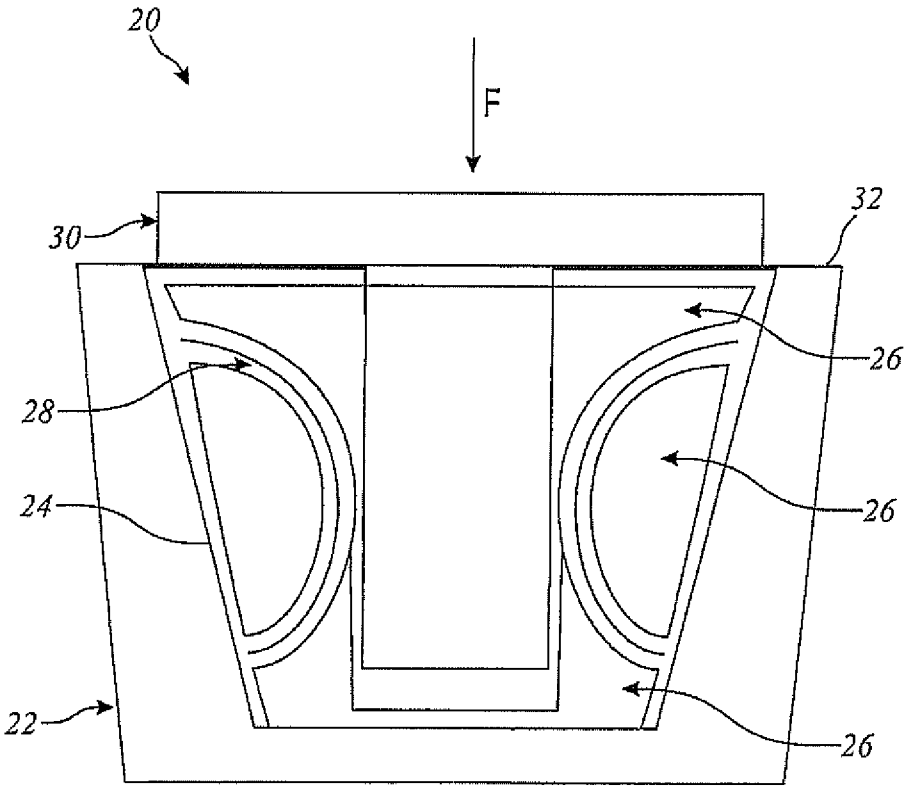
FIG. 5 is a schematic illustration of a compression tool according to an aspect of the present disclosure.

FIGS. 4-7 depict steps and schematically illustrate exemplary lamination processes. Referring to FIGS. 4 and 5, lamination method 200 can comprise obtaining a compression tool (202). As depicted in FIG. 5, a compression tool 20 can comprise compression tool body 22 defining a receptacle 24 including molded three-dimensional compliant tooling members 26 which are shaped to conform to the shape of the substrate. Compression tool 20 can also include lid 30 removably disposed on top surface 32 of compression tool body 22. Method 200 can further include placing the substrate 28 having the composite covering disposed thereon into the three-dimensional compliant mold (204) and applying heat and pressure to the lid via a heat press (206). The pressure and heat distribution within the compression tool can be directed radially using the inserts of the mold 26. Such pressure and heat can translate to the composite covering and substrate to laminate the composite covering to the substrate. The mold inserts 26 can be fabricated from a heat resistant, elastomeric material that is hard enough to exert pressure on the composite covering and the substrate. For example, the mold inserts can be fabricated from silicone or another soft material that does not approach its melting temperature at the temperature required to adhere the composite covering onto the substrate.

Figure 6:
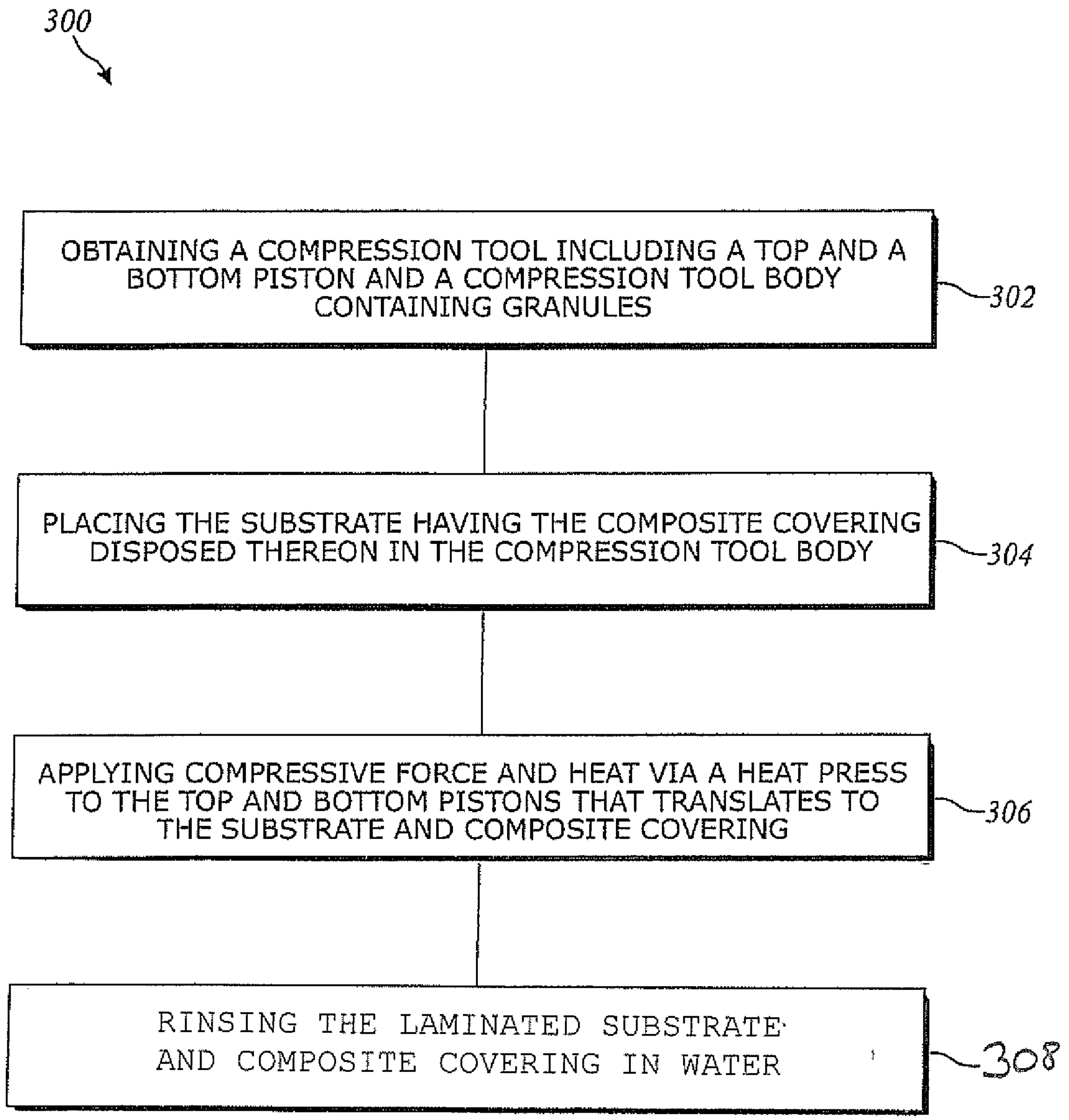
FIG. 6 is a block diagram of steps of an exemplary method of laminating a component of an insertable medical device to another component according to an aspect of the present disclosure.
Figure 7:
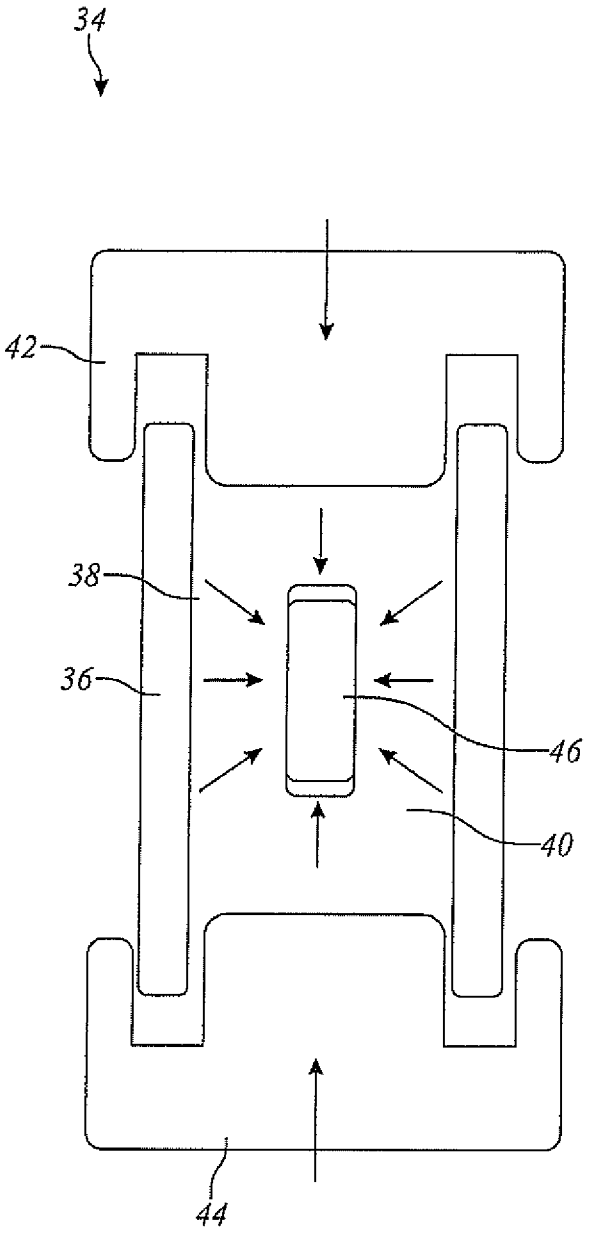
FIG. 7 is a schematic illustration of a compression tool according to an aspect of the present disclosure.

Referring to FIGS. 6 and 7, an alternative method 300 of laminating a composite covering onto a substrate comprises obtaining a compression tool (302). As shown in FIG. 7, a compression tool 34 can comprise a compression tool body 36 defining a receptacle 38 containing a fine, granular, inert, dry medium 40, such as for example, water-soluble sodium chloride or water-soluble calcium chloride. Compression tool 34 can further include top piston 42 slidably coupled to compression tool body 36 and bottom piston 44 slidably coupled to compression tool body 36. Either or both of top and bottom pistons can be removably coupled to the compression tool body. Method 300 can further include placing the substrate having the composite covering disposed thereon 46 into receptacle 38 (304) and applying compressive force and heat via a heat press to the top and bottom pistons (306) that translates through the fine, granular, inert, dry medium 40 to the substrate and the composite covering to laminate the composite covering to the substrate and thereby form an implantable medical device. In particular, medium 40 can impart compressive force and heat to the composite covering to achieve lamination and substrate adhesion. After the composite covering is laminated to the substrate, the at least one of the sodium chloride and calcium chloride is dissolved from the implantable medical device in a water rinse. Sodium chloride and calcium chloride are preferred because they can be finely subdivided into a stable powder, they do not affect the material in which they come in contact with, are biocompatible and non-toxic, and will dissolve away in water, leaving no residue. Rinsing the implantable medical device in water to dissolve the sodium chloride or calcium chloride is shown in step 114 in FIG. 3 and step 308 in FIG. 6.

The heat, both when using a compression tool with granules or a soft mold, comes from the heated press that heats up the outside of the compression tool. The pressure comes from the compressive forces applied to the compression body of the compression tool by the same heated press. Thus, in the molded insert-based compression tool, the molded insert elements transfer the heat and pressure applied to the outside of the compression tool to the inside of the compression tool to the substrate and composite covering. The molded insert elements can be designed to impart pressure in all directions inside the compression tool so that the longitudinal pressure can be redirected radially. Similarly, in the granule-based compression tool, the granules transfer the heat and pressure applied to the outside of the compression tool to the inside of the compression tool to the substrate and composite covering in all directions. Substrates, such as frames, usually cannot be touched by metal tooling, which is the typical material used to perform this kind of heat and pressure transfer in manufacturing of medical devices. Metallic tooling could very easily damage a stent frame so such a material cannot be used. Manufacturing methods as disclosed herein are advantageous in that metal tooling does not directly touch the substrate, such as a stent frame.

Alternatively, the substrate and composite covering can be loaded into a closed vessel and placed in an oven.

Each of the disclosed aspects and embodiments of the present disclosure may be considered individually or in combination with other aspects, embodiments, and variations of the disclosure. Unless otherwise specified, none of the steps of the methods of the present disclosure are confined to any particular order of performance.

What is claimed is:

1. A method, comprising the steps of:

a) providing a substrate comprising a metallic or polymeric material, the substrate having a plurality of spaces extending to and defined by an inner substrate surface spaced from an outer substrate surface;

b) providing a textile fabric layer and heat stabilizing the textile fabric layer;

c) coating the heat stabilized textile fabric layer with a thermoplastic polymer to thereby form a textile fabric composite covering;

d) obtaining a compression tool, comprising:

i) a compression tool body defining a receptacle, the receptacle including a granular, inert, water-soluble medium;

ii) a top piston slidably coupled to the compression tool body; and iii) a bottom piston slidably coupled to the compression tool body;

e) conformally contacting the textile fabric composite covering to at least one of the inner substrate surface and the outer substrate surface;

f) placing the substrate having the composite covering disposed thereon into the receptacle; and g) applying compressive force and heat to the top and bottom pistons via a heat press that translates through the granular, inert, water-soluble medium to laminate the textile fabric composite covering to the at least one of the inner substrate surface and the outer substrate surface.

2. The method of claim 1, including, after the textile fabric composite covering is laminated to at least one of the inner substrate surface and the outer substrate surface, rinsing the textile fabric composite covering laminated to the substrate in water to dissolve the granular, inert, water-soluble medium, thereby forming an implantable medical device.

3. The method of claim 1, including condensing the textile fabric layer prior to coating the textile fabric layer with the thermoplastic polymer.

4. The method of claim 3, including providing the top and bottom pistons of the compression tool comprising silicone.

5. The method of claim 1, including, during the heat press, heating the substrate having the textile fabric composite covering disposed thereon to a temperature that is above the glass transition temperature of the thermoplastic polymer to laminate the textile fabric composite covering to the at least one of the inner substrate surface and the outer substrate surface.

6. The method of claim 1, including, before placing the substrate having the textile fabric composite covering disposed thereon into the receptacle of the compression tool, contacting a silane cross-linkage material to the at least one of the inner substrate surface and the outer substrate surface so that the textile fabric composite covering is attached to the silane cross-linkage material contacted to the substrate.

7. The method of claim 1, including providing the textile fabric composite covering comprising the thermoplastic polymer coating the textile fabric layer having a total thickness that ranges from about 15 μm and about 250 μm.

8. The method of claim 1, including laminating the textile fabric composite covering to less than the entire at least one of the inner substrate surface and the outer substrate surface.

9. The method of claim 1, including providing the textile fabric composite covering having an anti-thrombogenic surface.

10. The method of claim 1, including selecting the textile fabric layer from a knit monofilament yarn, a knit multifilament yarn, a woven monofilament yarn, a woven multifilament yarn, a braided monofilament yarn, and a braided multifilament yarn.

11. The method of claim 10, including providing the knit monofilament yarn, the knit multifilament yarn, the woven monofilament yarn, the woven multifilament yarn, the braided monofilament, or the braided multifilament yarn of the textile fabric layer having a tenacity that ranges from about 3-gram denier to about 10-gram denier.

12. The method of claim 1, including selecting the textile fabric layer from an implantable grade resorbable polymer yarn, a non-resorbable polymer yarn, and a mixture of resorbable and non-resorbable polymer yarns.

13. The method of claim 10, including extruding the monofilament yarn or the multifilament yarn from a PET polyester, a polypropylene, a polyurethane, a polytetrafluoroethylene, an ultra-high-molecular-weight polyethylene, a regenerated silk, a nylon, a liquid crystal polymer, a polyether block amide, and combinations thereof.

14. The method of claim 10, including twisting the multifilament yarn comprising the knit multifilament yarn, the woven multifilament yarn, or the braided multifilament yarn.

15. The method of claim 1, including selecting the thermoplastic polymer of the textile fabric composite covering from a thermoplastic polyurethane, a silicone elastomer, a polyurethane-silicone co-polymer, a polytetrafluoroethylene, a fluorinated ethylene/propylene, a perfluoroalkoxy fluorocarbon, an ethylene/tetrafluoroethylene copolymer, a polycarbonate urethane, a polyethylene, a polyamide, a polyimide, a polyester, a polypropylene, a polyfluoroethylene, a fluorinated polyolefin, a fluorinated ethylene copolymer, a polyvinylpyrrolidone, a lactide, glycolide, a caprolactone, a polyhydroxybutyrate, a polydioxanone, and combinations thereof.

16. The method of claim 1, including roughening the at least one of the inner substrate surface and the outer substrate surface before laminating the textile fabric composite covering to the substrate.

17. The method of claim 1, including selectively leaving a portion of the textile fabric layer uncoated with the thermoplastic polymer.

18. The method of claim 1, including providing the substrate having a shape of a heart valve repair or replacement device with the inner substrate surface defining a lumen extending therethrough.

19. The method of claim 1, including providing the compression tool comprising a three-dimensional compliant mold shaped to conform to a shape of the substrate.

* * * * *